(12) United States Patent
Schuessler

(10) Patent No.: US 6,419,699 B1
(45) Date of Patent: Jul. 16, 2002

(54) UNIVERSAL IMPLANT FILL CONNECTOR

(75) Inventor: David J. Schuessler, Ventura, CA (US)

(73) Assignee: McGhan Medical Corporation, Santa Barbara, CA (US)

( * ) Notice: Subject to any disclaimer, the term of this patent is extended or adjusted under 35 U.S.C. 154(b) by 0 days.

(21) Appl. No.: 09/291,547

(22) Filed: Apr. 14, 1999

(51) Int. Cl.[7] .............................. A61F 2/02; A61F 2/66; A61B 17/08
(52) U.S. Cl. .................... 623/11.11; 606/151; 606/153; 604/905; 623/48
(58) Field of Search ........................... 623/11.11, 16.11, 623/48; 606/151, 153; 604/905, 283; 141/387, 392; 137/615, 616, 616.3; 285/261

(56) References Cited

U.S. PATENT DOCUMENTS

| | | |
|---|---|---|
| 2,564,938 A | 8/1951 | Warren |
| 2,890,067 A | 6/1959 | Morin |
| 3,475,039 A | 10/1969 | Ortloff |
| 4,035,004 A | 7/1977 | Hengesbach |
| 4,056,116 A | 11/1977 | Carter et al. |
| 4,178,643 A | 12/1979 | Cox, Jr. |
| 4,427,218 A | 1/1984 | Duvet et al. |
| 4,662,396 A | 5/1987 | Avnon |
| 4,787,882 A | 11/1988 | Claren |
| 4,852,564 A | 8/1989 | Sheridan et al. |
| 4,875,718 A | 10/1989 | Marken |
| 5,114,033 A | 5/1992 | Golias et al. |
| 5,146,933 A | 9/1992 | Boyd |
| 5,507,536 A | 4/1996 | Oliveto, II et al. |
| 5,533,983 A | 7/1996 | Haining |
| 5,645,539 A | * 7/1997 | Solomon et al. ............ 604/283 |
| 5,651,773 A | * 7/1997 | Perry et al. ................. 604/174 |
| 5,899,944 A | 5/1999 | Phillips |
| 5,975,490 A | 11/1999 | Essman |

* cited by examiner

*Primary Examiner*—Corrine McDermott
*Assistant Examiner*—Alvin Stewart
(74) *Attorney, Agent, or Firm*—Milbank, Tweed, Hadley & McCloy LLP

(57) ABSTRACT

A universal implant fill connector for coupling a fill tubing to an implant is disclosed. A barb, or other leakproof fill tubing connection, couples to the fill tubing, and a fill tip couples to the implant. The barb and the fill tip each have a passage therethrough, and each of these passages have an axis. A joint connects the barb to the fill tip so that said barb may rotate from a position where the barb axis is approximately parallel to the fill tip axis to a position where the barb axis is approximately perpendicular to the fill tip axis. Another form of the disclosed connector includes a joint that connects the barb to the fill tip so that the barb may rotate approximately 360 degrees about the fill tip axis.

12 Claims, 6 Drawing Sheets

UNIVERSAL IMPLANT FILL CONNECTOR

BACKGROUND OF THE INVENTION

1. Field of the Invention

The present invention relates to a universal implant fill connector which allows a range of angular motion between the fill tubing and the implant.

2. Description of the Related Art

In various surgical procedures, an implant is placed within a body cavity for subsequent inflation and/or deflation with a fluid.

In plastic and reconstructive surgery, when a breast implant or tissue expander is placed in the dissected pocket, it is typically filled via a fill connector coupled to fill tubing which is attached to a filling material (e.g. saline solution) source. Another example is bariatric surgery where a gastric balloon or gastric band is implanted in or around the stomach for subsequent inflation.

There are currently three basic types of fill connectors used to connect the fluid source to the implant, the choice of which often depends on the implant and the particular surgical approach used. The first is a permanent attachment of the fill tubing to the implant. A common means for this attachment is to make a small opening within the body or shell of the implant and insert the tubing securing it by means of connecting materials such as sleeves, patch assemblies, adhesives or vulcanizing compounds.

The other two common connectors are for temporary attachment of the fill tubing to the implant by means of a valve in the implant which seals after the fill tubing is removed. One of these two temporary attachment means is most commonly used with saline-fill breast implant devices that include a diaphragm valve within the shell. The valve has an opening that requires a rigid male implement to be inserted in the opening thus opening the valve and allowing fluid transfer. This male implement is the fill tip end of the fill connector, which has on the opposite end one or more barbs which accept the flexible (e.g. silicone or vinyl) fill tubing. In use, the fill connector and fill tubing attach to the implant normal to the implant surface.

The other of the two connectors for temporary fill tubing attachment is designed for a leaf valve which consists of parallel sheets of material forming a channel along the surface of the implant into which a cannula or stylet may be inserted. When this valve is engaged, the fill tubing is generally tangent to the implant surface. In breast implant surgery where typically the fill tubing is a temporary attachment, a surgical approach using either the normal or tangential fill tube orientation is selected before the surgical procedure commences. As a result, an ad-hoc determination of which approach to use, which may be necessary because of unexpected developments that arise prior to or during the surgical procedure, is currently impossible. Thus, an accurate analysis,of which surgical approach is best suited to a particular patient's particular need is necessary before surgery may proceed.

Placement of implants in body cavities is usually performed without visual assistance and in small pockets or within dissected tissue planes. Implant orientation with respect to the tubing position and body opening cannot always be ascertained. Complications can arise because of blocked or kinked tubing or premature detachment of the fill tubing from the implant due to excessive tangential and torsional forces on the inflexible connections. Difficulty in filling, improper fill volume, or inability to complete the filling procedure can all delay surgery, require explant, or require surgery to be aborted.

It is desirable to provide a filling system that can be used for surgical applications calling for either normal or tangential placement of the fill tubing in order to eliminate the requirement for time-consuming analysis before surgery and the potential complications of inflexibly oriented connections during surgery. Thus multiple valves and/or multiple fill tubing geometries may be provided with each implant (i.e. provide both a typical straight fill connector and a 90 degree "L" fill connector). This solution, however, still requires multiple product inventories and predetermined patient needs regarding the surgical approach used.

SUMMARY OF THE INVENTION

A fill connector could be modified at its barbed, or leakproof fill tubing connection, end to resolve these intraoperative problems and be universally adaptable for any implant or surgical approach. Several design possibilities exist but all entail incorporating a multi-directional connecting means to the implant. Any of these designs would be constructed out of commonly used biocompatible materials, i.e., plastics/elastomers, preferably those compatible with common sterilization processes.

One particular embodiment includes a fill connector with a ball-joint connection having a leak proof fluid pathway therethrough such that the fill tubing may be rotated anywhere from tangential (approximately 0 degrees) to the implant surface up to normal (approximately 90 degrees) to the implant surface.

In a another embodiment, the ball-joint connection could also allow for 360 degree rotation of the fill tubing about an axis approximately normal to the implant surface (i.e., in the plane parallel to the surface of the implant).

An alternative to the ball-joint approach is to use a softer, more flexible material at the barbed end of a typical straight fill connector, while maintaining the standard material (typically polypropylene) at the valve engaging end.

Yet another alternative embodiment is to design the connector with a bellows having accordion-like pleats and appropriately thinner wall sections to allow ease of bending and repeatable multi-directional flexing.

BRIEF DESCRIPTION OF THE DRAWINGS

The invention will be more clearly described by way of reference to the accompanying drawings, wherein.

DETAILED DESCRIPTION OF THE DRAWINGS

Embodiments of the invention will be described in detail with reference to the accompanying drawings.

Figure 1A:
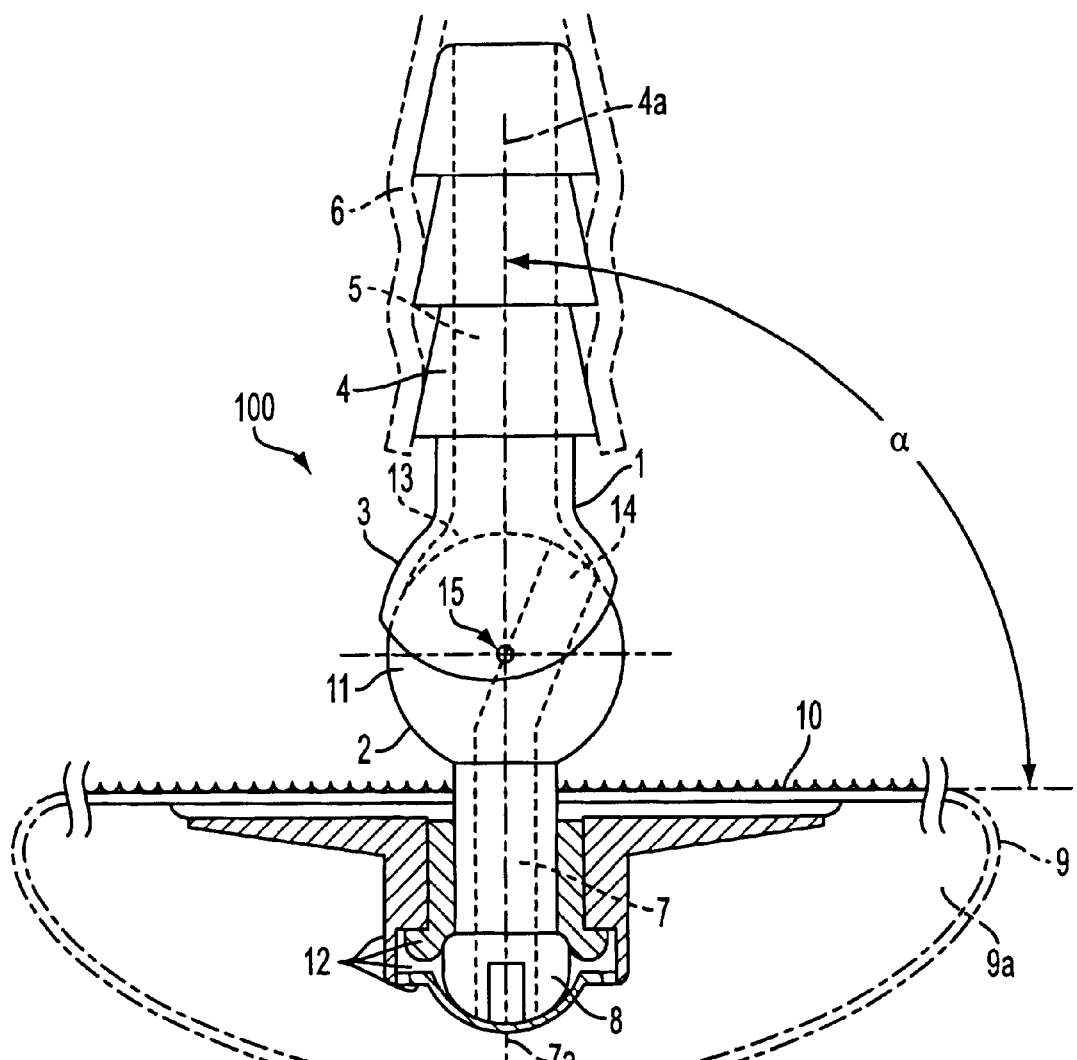
FIGS. 1a and 1b are is a cross-sectional side view of a ball-joint embodiment of the invention.
Figure 1B:
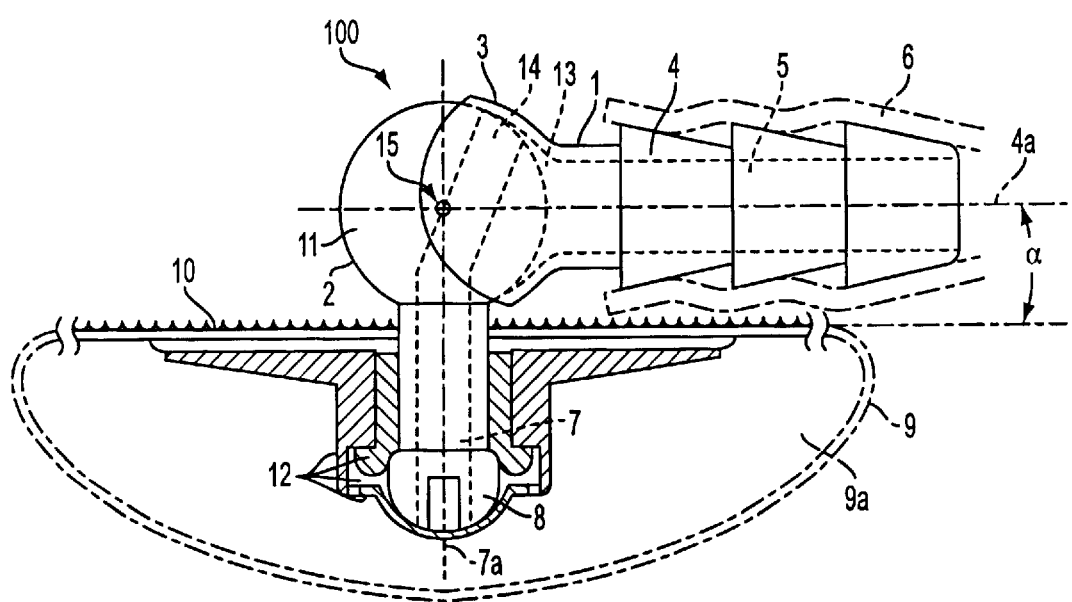

FIGS. 1a and 1b show a fill connector which allows the fill tubing to rotate from a normal position, approximately perpendicular to the implant surface (FIG. 1a), to a tangent position, approximately parallel to the implant surface (FIG.

1b). The fill connector 100 is formed of barb member 1 and fill tip member 2. The socket 3 of barb member 1 is rotatably coupled around pivot 15 to the ball 11 of fill tip member 2. During use, fill tubing 6 is coupled to barb member 1 using a conventional pipe barb 4. The bulb 8 of fill tip member 2 is inserted into diaphragm valve 12 of implant 9.

The barb member 1 and fill tip member 2 may be rotated with respect to each other so that the angle α between the barb axis 4a of barb 4 and the surface 10 of implant 9 may range from about 0° (approximately tangent as shown in FIG. 1b) to about 90° (approximately normal, as shown in FIG. 1a). Thus, the connector 100 may be rotated between a position where barb axis 4a is approximately perpendicular to the fill tip axis 7a and a position where barb axis 4a is approximately parallel to fill tip axis 7a. In a preferred embodiment, the dimensions of the connector are such that when α is approximately 0°, the overall projection of the connector (as measured from and normal to the implant surface 10) is minimized, and the outer surface of fill tubing 6 rests upon implant surface 10.

Socket passage 13 and ball passage 14 are shaped so that there is a sufficient sealing surface between socket 3 and ball 11 to provide a path that is leak proof at both the negative and positive pressures exerted during the implant fill process.

During use, air is evacuated from implant chamber 9a through fill tip passage 7, ball passage 14, socket passage 13, barb passage 5, and through fill tubing 6. Similarly, the implant filling material flows from fill tubing 6 through barb passage 5, socket passage 13, ball passage 14, and fill tip passage 7 into implant chamber 9a.

The sealing surfaces of the ball 11 and socket 3 as well as the ball passage 14 and socket passage 13 may be designed to allow rotation about the fill tip axis. Furthermore, at pivot 15, the ball 11 and socket 3 may be provided with indentations and corresponding projections which allow the ball and socket to be lockable at different angles. As an alternative to the embodiment shown in FIGS. 1a and 1b, the connector may be designed so that the ball is part of the barb member, and the socket is part of the fill tip member.

Figure 2A:
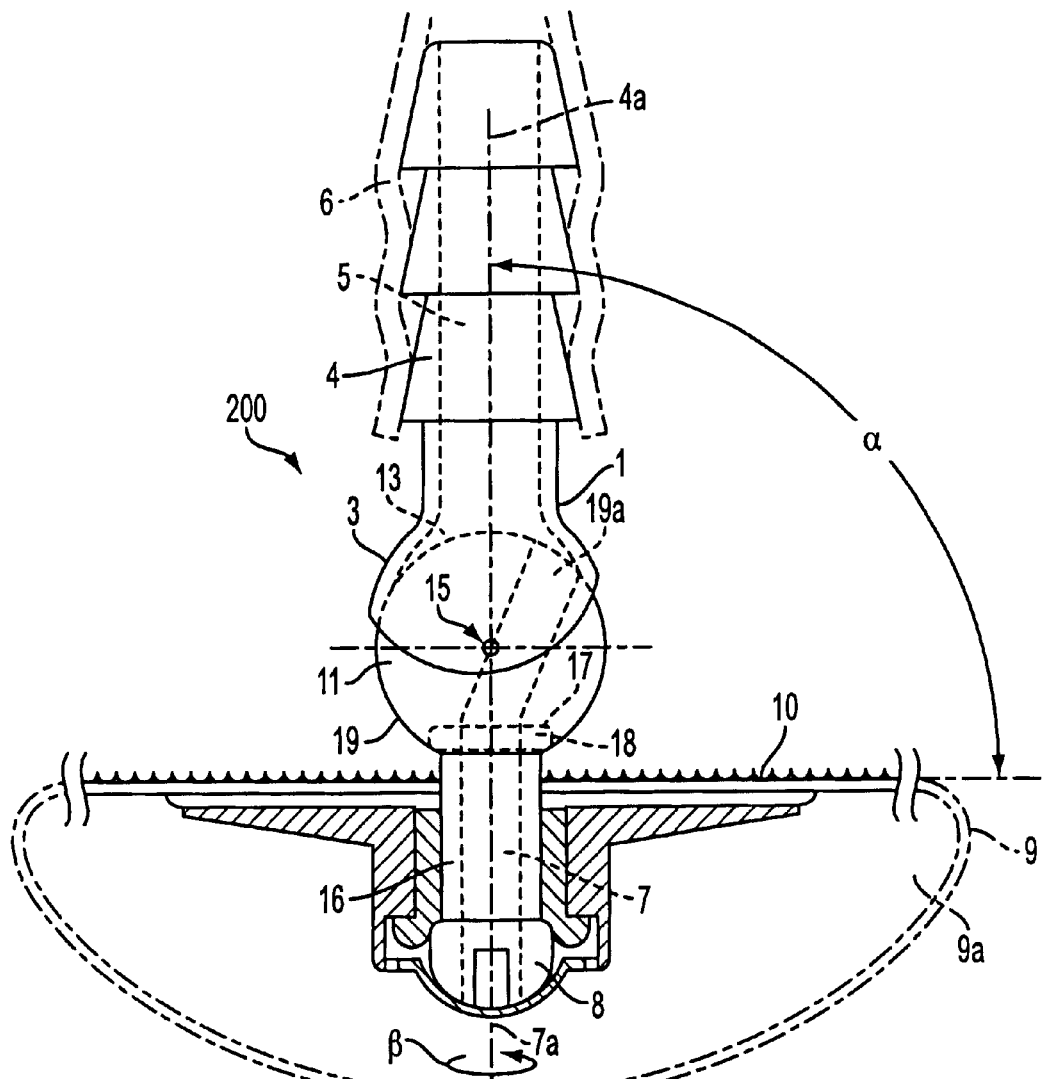
FIGS. 2a and 2b are a cross-sectional side view of a modified ball-joint embodiment of the invention which includes a swivel joint which allows 360 degree rotation about an axis approximately normal to the implant surface.
Figure 2B:
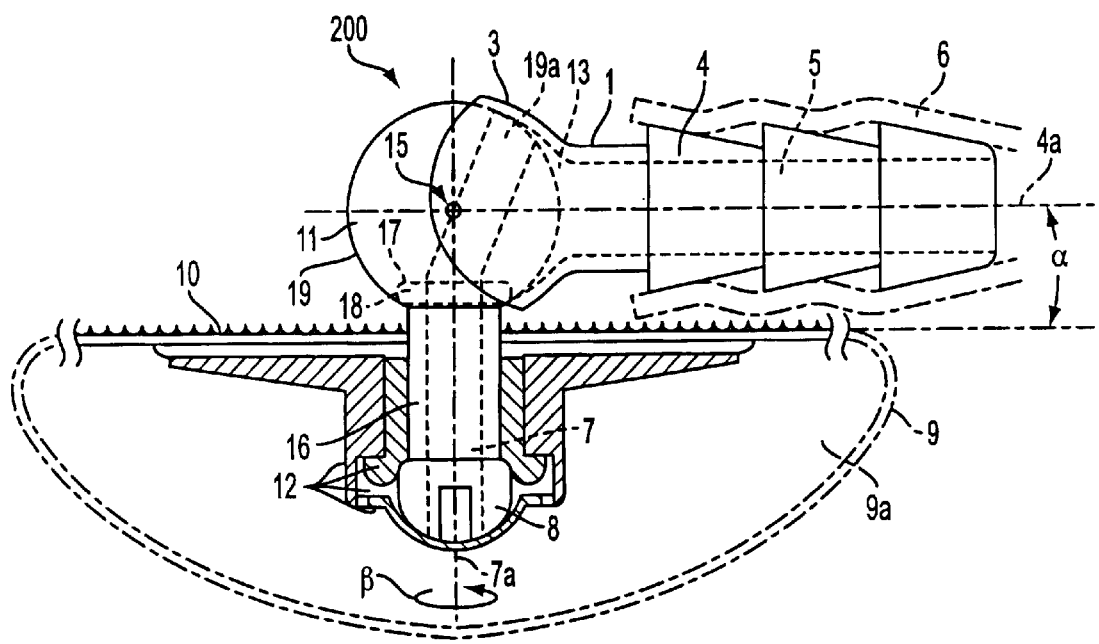

FIGS. 2a and 2b show a modification of the fill connector embodiment described above which includes the function and structure of the rotatable ball-and-socket connector described above as well as including additional structure which allows rotation about an axis normal to the implant surface. The fill connector 200 is formed of barb member, 1, swivel member 19, and fill tip member 16. Similar to that described above, the socket 3 of barb member 1 is rotatably coupled to the ball 11 of swivel member 19. During use, fill tubing 6 is coupled to barb member 1 using barb 4. As used herein, the term "barb" refers to any such conventional pipe barb or any appropriate mechanical, chemical, or thermal joint between the :connector and the fill tubing which provides a leakproof connection at both the negative and positive pressures exerted during the implant fill process. The bulb 8 of fill tip member 16 is inserted into diaphragm valve 12 of implant 9.

Similar to the embodiment described above, the barb member 1 and swivel member 19 may be rotated with respect to each other so that the angle α between the barb axis 4a of barb 4 and the surface 10 of implant 9 may range from about 0° (approximately tangent, as shown in FIG. 2b) to about 90° (approximately normal, as shown in FIG. 2a). Thus, the connector 200 may be rotated between a position where barb axis 4a is approximately perpendicular to the fill tube axis 7a and a position where barb axis 4a is approximately parallel to the fill tube axis 7a. In addition, the swivel member 19 and the fill tip member 16 may be rotated with respect to each other so that the angle β between the relative positions of the swivel member 19 and the fill tip member 16, around the fill tip axis 7a, may have a range of about 360°.

Also similar to that described above, socket passage 13 and ball passage 14 are shaped so that there is a sufficient sealing surface between socket 3 and ball 11 to provide a leak-proof path. In addition, swivel member sealing structure 17 and fill tip member sealing structure 18 are shaped to provide a swivel joint that is leak proof at both the negative and positive pressures exerted during the implant fill process. As shown in FIGS. 2a and 2b, the swivel member sealing structure 17 may be a cylindrical indentation which acts as the external rotor of the swivel joint, and fill tip sealing structure 18 may be a cylindrical projection which acts as the internal stator of the swivel joint, or the swivel joint may be implemented so that the rotor and stator are conversely positioned, i.e., the swivel member sealing structure is located within the fill tip member sealing structure.

During use, air is evacuated from implant chamber 9a through fill tip passage 7, swivel member passage 19a, socket passage 13, barb passage 5, and through fill tubing 6. Similarly, the implant filling material flows from fill tubing 6 through barb passage 5, socket passage 13, swivel member passage 19a, and fill tip passage 7 into implant chamber 9a.

Figure 3:
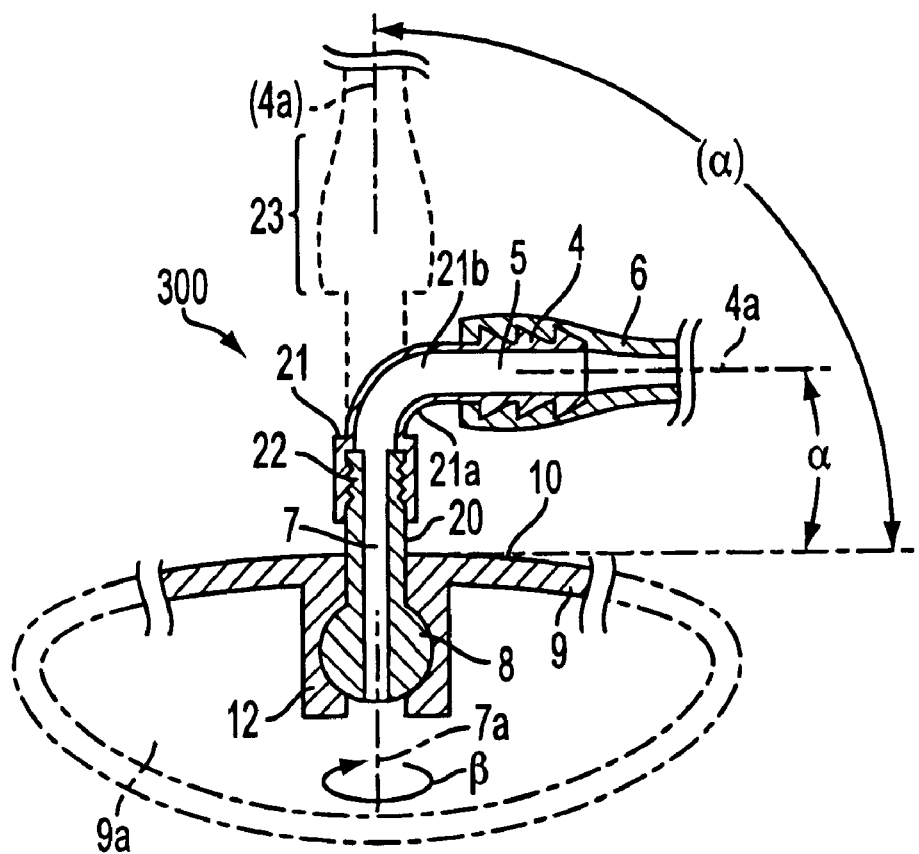
FIG. 3 is a side view of a flexible-tube embodiment of the invention.

Another embodiment of the invention is illustrated in FIG. 3, which shows a flexible-tube fill connector which allows the fill tubing to be rotated from a tangent position, approximately parallel to the implant surface, to a normal position, approximately perpendicular to the implant surface. This embodiment also allows the fill tubing to be rotated about an axis normal to the implant surface. The fill connector 300 is formed of barb member 21 and fill tip member 20. Fill tip member 20 is made of a rigid material (e.g., polypropylene), and barb member 21 is made of a softer, more flexible material. Fill tip member 20 and barb member 21 are rigidly connected at joint 22. Joint 22 may be made using any appropriate mechanical or thermal process which provides a leak-proof seal at both the negative and positive pressures exerted during the implant fill process. During use, fill tubing 6 is coupled to barb member 21 by barb 4. The bulb 8 of fill tip member 20 is inserted into diaphragm valve 12 of implant 9.

The barb member 20 and fill tip member 21 may be rotated with respect to each other by flexing tube portion 21a of barb member 21 so that the angle a between the barb axis 4a of barb 4 and the surface 10 of implant 9 may range from about 0° (approximately tangent) to about 90° (approximately normal). Outline 23 shows the location of barb member 21 and fill tubing 6 when they are rotated into a position where α is equal to approximately 90°. Consequently, connector 300 may be rotated between a position where barb axis 4a is approximately perpendicular to fill tip axis 7a and a position where barb axis 4a is approximately parallel to fill tip axis 7a. In addition, the barb member 20 and fill tip member 21 may be rotated with respect to each other by flexing tube portion 21a of barb member 21 so that the angle β between the relative positions of the barb member 21 and the fill tip member 21, around the fill tip axis 7a, may have a range of about 360°.

During use, air is evacuated from implant chamber 9a through fill tip passage 7, tube portion passage 21b, barb passage 5, and through fill tubing 6. Similarly, the implant filling material flows from fill tubing 6 through barb passage 5, tube portion passage 21b, and fill tip passage 7 into implant chamber 9a.

Figure 4:
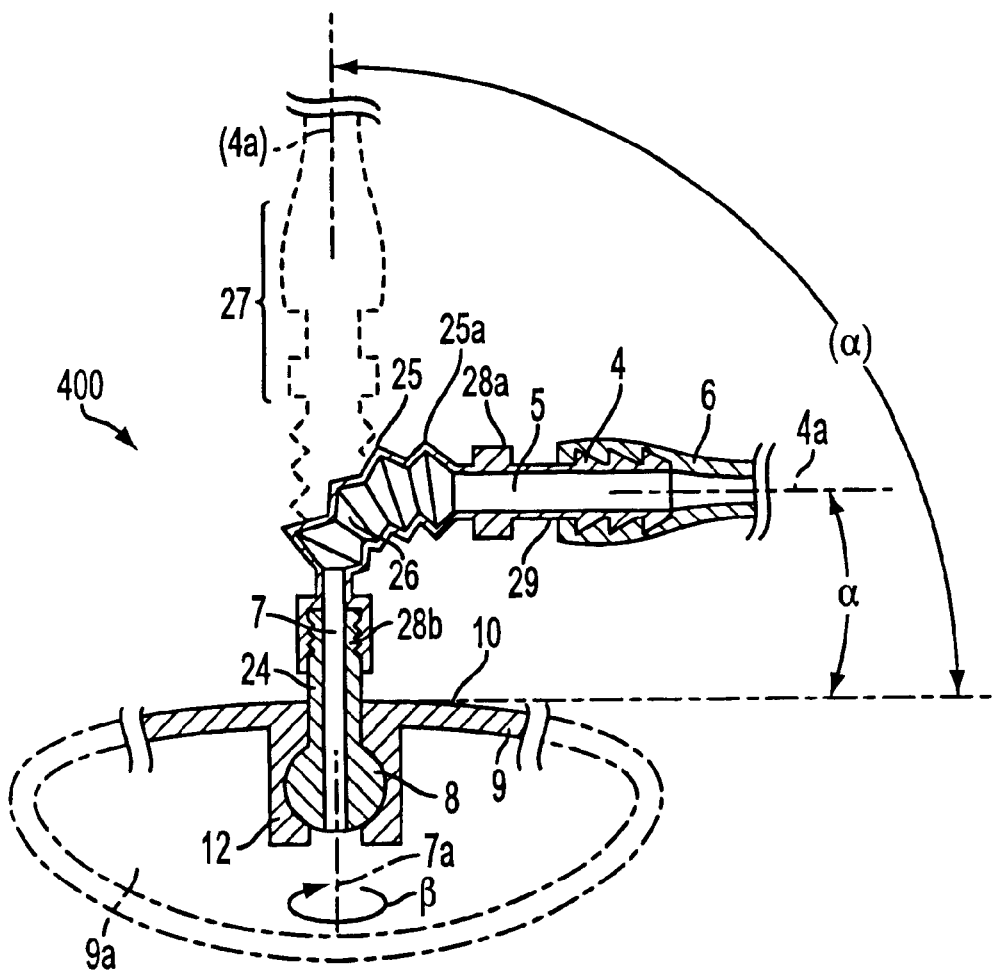
FIG. 4 is a side view of a bellows embodiment of the invention.

A further embodiment of the invention is shown in FIG. 4, which shows a bellows fill connector which allows the fill tubing to be rotated from a tangent position, approximately parallel to the implant surface, to a normal position, approximately perpendicular to the implant surface. This embodiment also allows rotation of the fill tubing about an axis normal to the implant surface. In this embodiment, the fill connector 400 is formed of barb member 29, bellows 25, and fill tip member 24. Bellows 25 includes a wall thickness 25a and pleats 25b which allow repeated multi-directional bending and flexing. Barb member 29 and bellows 25 are connected at joint 28a, and fill tip member 24 and bellows 25 are connected at joint 28b. Joints 28a and 28b may be made using any appropriate mechanical or thermal process which provides a leak-proof seal at both the negative and positive pressures exerted during the implant fill process. Alternatively, of barb member 29, bellows 25, and fill tip member 24 may be a single-piece molding. During use, fill tubing 6 is coupled to barb member 29 by barb 4. The bulb 8 of fill tip member 24 is inserted into diaphragm valve 12 of implant 9.

The barb member 29 and fill tip member 24 may be rotated with respect to each other by flexing bellows 25 so that the angle α between the barb axis 4a of barb 4 and the surface 10 of implant 9 may range from about 0° (approximately tangent) to about 90° (approximately normal). Outline 27 shows the location of barb member 29, bellows 25, and fill tubing 6 when they are rotated into a position where α is equal to approximately 90°. Consequently, connector 400 may be rotated between a position where barb axis 4a is approximately perpendicular to fill tip axis 7a and a position where barb axis 4a is approximately parallel to fill tip axis 7a. In addition, the barb member 29 and fill tip member 24 may be rotated with respect to each other by flexing bellows 25 so that the angle β between the relative positions of the barb member 29 and the fill tip member 24, around the fill tip axis 7a, may have a range of about 360°.

During use, air is evacuated from implant chamber 9a through fill tip passage 7, bellows passage 26, barb passage 5, and through fill tubing 6. Similarly, the implant filling material flows from fill tubing 6 through barb passage 5, bellows passage 26, and fill tip passage:7 into implant chamber 9a.

The present invention has been described with respect to particular illustrative embodiments. It is to be understood that the invention is not limited to the above-described embodiments, and that various changes and modifications may be made by those of ordinary skill in the art without departing from the spirit and scope of the appended claims.

What is claimed is:

1. A universal implant fill connector for coupling a fill tubing to an implant, comprising:
    a barb for coupling to the fill tubing, said barb having a passage therethrough, said barb passage having a barb axis;
    a fill tip for coupling to the implant, said fill tip having a passage therethrough, said fill tip passage having a fill tip axis; and
    a ball-and-socket joint for coupling said barb to said fill tip so that said barb may be rotated through an angular range from a first position where said barb axis is approximately parallel to said fill tip axis to a second position where said barb axis is approximately perpendicular to said fill tip axis.

2. The connector as claimed in claim 1, wherein a ball and a socket of said ball-and-socket joint are lockable at a position within said angular range.

3. A universal implant fill connector for coupling a fill tubing to an implant, comprising:
    a barb for coupling to the fill tubing, said barb having a passage therethrough, said barb passage having a barb axis;
    a fill tip for coupling to the implant, said fill tip having a passage therethrough, said fill tip passage having a fill tip axis; and
    a joint for coupling said barb to said fill tip so that said barb may be rotated through an angular range from a first position where said barb axis is approximately parallel to said fill tip axis to a second position where said barb axis is approximately perpendicular to said fill tip axis, and so that so that said barb may be rotated approximately 360 degrees about said fill tip, said joint including a ball-and-socket joint.

4. The connector as claimed in claim 3, wherein a ball and a socket of said ball-and-socket joint are lockable at a position within said angular range.

5. The connector as claimed in claim 3, wherein said joint comprises a swivel joint.

6. A universal implant fill connector for coupling a fill tubing to an implant, comprising:
    means for coupling the connector to the fill tubing, said fill tubing coupling means having a fill tubing coupling axis;
    means for coupling the connector to the implant, said implant coupling means having an implant coupling axis; and
    means for joining said fill tubing coupling means to said implant coupling means so that said fill tubing coupling means may be rotated from a first position where said fill tubing coupling axis is approximately parallel to said implant coupling axis to a second position where said fill tube coupling axis is approximately perpendicular to said implant coupling axis, said means for coupling including a ball-and-socket joint.

7. The connector as claimed in claim 6, wherein said connector further comprises
    means for joining said fill tubing coupling means to said implant coupling means so that said fill tubing coupling means may be rotated approximately 360 degrees about said implant coupling axis.

8. A method of connecting a fill tubing to an implant, comprising:
    coupling a barb to the fill tubing, said barb having a passage therethrough, said barb passage having a barb axis,
    coupling a fill tip to the implant, said fill tip having a fill tip passage therethrough, said fill tip passage having a fill tip axis; and coupling said barb to said fill tip so that said barb may be rotated through an angular range from a first position where said barb axis is approximately parallel to said fill tip axis to a second position where said barb axis is approximately perpendicular to said fill tip axis, said coupling including coupling a ball and a socket of a ball-and-socket joint.

9. The method as claimed in claim 8, further comprising the step of locking said ball and said socket at a position within said angular range.

10. The method as claimed in claim 8, further comprising: coupling said barb to said fill tip so that said barb may rotate approximately 360 degrees about said fill tip axis.

11. The connecting method as claimed in claim 10, further comprising the step of locking said ball and said socket at a position within said angular range.

12. The connecting method as claimed in claim 10, wherein said barb and fill tip coupling step further comprises coupling a rotor and a stator of a swivel joint.

* * * * *